United States Patent
Wax et al.

(10) Patent No.: US 9,335,154 B2
(45) Date of Patent: May 10, 2016

(54) SYSTEMS AND METHODS OF ANGLE-RESOLVED LOW COHERENCE INTERFEROMETRY BASED OPTICAL CORRELATION

(71) Applicant: Duke University, Durham, NC (US)

(72) Inventors: Adam P. Wax, Chapel Hill, NC (US); Michael G. Giacomelli, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/170,957

(22) Filed: Feb. 3, 2014

(65) Prior Publication Data

US 2014/0218748 A1  Aug. 7, 2014

Related U.S. Application Data

(60) Provisional application No. 61/759,635, filed on Feb. 1, 2013.

(51) Int. Cl.
| | |
|---|---|
| *G01B 11/02* | (2006.01) |
| *G01B 9/02* | (2006.01) |
| *A61B 3/10* | (2006.01) |

(52) U.S. Cl.
CPC .......... *G01B 9/0209* (2013.01); *G01B 9/02041* (2013.01); *G01B 9/02043* (2013.01); *G01B 9/02044* (2013.01); *G01B 9/02091* (2013.01); *A61B 3/102* (2013.01)

(58) Field of Classification Search
CPC ............ G01B 9/02038; G01B 9/0209; G01B 9/02091
USPC .................................................. 356/497, 479
See application file for complete search history.

(56) References Cited

U.S. PATENT DOCUMENTS

| | | | | |
|---|---|---|---|---|
| 7,551,293 B2 * | 6/2009 | Yelin et al. | .................... | 356/497 |
| 8,537,366 B2 | 9/2013 | Wax et al. | | |
| 2004/0223162 A1 * | 11/2004 | Wax | .............................. | 356/497 |
| 2007/0201033 A1 * | 8/2007 | Desjardins et al. | ........... | 356/497 |

* cited by examiner

*Primary Examiner* — Jonathan Hansen
(74) *Attorney, Agent, or Firm* — Olive Law Group, PLLC (57) ABSTRACT

Systems and methods of angle-resolved low coherence interferometry based optical correlation are disclosed. According to an aspect, a method includes directing a sample beam towards a sample for producing a scattered sample beam from the sample. The method also includes receiving the scattered sample beam at a multitude of scattering angles in at least two directions. Further, the method includes cross-correlating the scattered sample beam with a reference beam to produce a two-dimensional angle and depth resolved profile of the sample scattered beam. The method also includes processing the two-dimensional angle and depth scattered profile to obtain correlated information about scattering structures in the sample.

22 Claims, 10 Drawing Sheets

SYSTEMS AND METHODS OF ANGLE-RESOLVED LOW COHERENCE INTERFEROMETRY BASED OPTICAL CORRELATION

CROSS REFERENCE TO RELATED APPLICATION

This application claims the benefit of U.S. Provisional Patent Application No. 61/759,635, filed Feb. 1, 2013 and titled SYSTEMS AND METHODS FOR MEASUREMENT OF ARCHITECTURE OF BIOLOGICAL MEDIA USING ANGLE-RESOLVED LOW COHERENCE INTERFEROMETRY-BASED OPTICAL CORRELATION, the disclosure of which is incorporated herein by reference in its entirety.

TECHNICAL FIELD

The presently disclosed subject matter relates to imaging. Particularly, the presently disclosed subject matter relates to systems and methods of angle-resolved low coherence interferometry based optical correlation.

BACKGROUND

Spectral domain optical coherence tomography (SDOCT) has been used for assessing structural changes associated with retinal degenerative diseases. However, while SDOCT can resolve histological layers, it lacks the resolution to measure cellular features. In recent SDOCT studies, only a modest correlation between the thickness of the retinal nerve fiber layer and the progression of glaucoma has been shown, with similar findings seen between the thickness of the photoreceptor layer and progression of retinitis pigmentosa. This reflects the fact that thickness of an individual retina layer does not necessarily correlate with the health or anatomical condition of its constituent cells.

Direct imaging of cellular features can allow detection of degenerative conditions based on changes in cellular structure or composition. However, practical retinal imaging systems, such as SDOCT and scanning laser ophthalmoscopy (SLO) achieve a factor of 5-10 fold lower resolution than is required for cellular resolution because imperfections in the human eye lens introduce random phase errors in transmitted light that blur out fine image details. A complementary technology, adaptive optics (AO), uses wavefront sensing techniques to measure aberrations caused by imperfections in the eye. This information may then be used as input to a correction approach, such as a deformable mirror, to correct for these aberrations.

However, the use of AO comes at a very large increase in system cost and complexity. AO imaging of awake human patients requires real time wavefront sensing and correction with subwavelength accuracy on a millisecond time scale in response to patient movement. This represents a formidable engineering challenge. From the clinical perspective, the high cost of AO is likely to preclude its widespread use in screening patients for retinal disease. Consequently, there is a significant need for improved systems and techniques for retrieving information about the health and organization of retinal layers and similar sample features.

BRIEF SUMMARY

Disclosed herein are systems and methods of angle-resolved low coherence interferometry based optical correlation. According to an aspect, a method includes directing a sample beam towards a sample for producing a scattered sample beam from the sample. The method also includes receiving the scattered sample beam at a multitude of scattering angles in at least two directions. Further, the method includes cross-correlating the scattered sample beam with a reference beam to produce a two-dimensional angle and depth resolved profile of the sample scattered beam. The method also includes processing the two-dimensional angle and depth scattered profile to obtain correlated information about scattering structures in the sample.

BRIEF DESCRIPTION OF THE SEVERAL VIEWS OF THE DRAWINGS

The foregoing aspects and other features of the present subject matter are explained in the following description, taken in connection with the accompanying drawings, wherein:

FIG. 4B shows a confocal fluorescence image showing the same tissue showing cell nuclei and an antibody targeting peripheral nervous tissue;

DETAILED DESCRIPTION

For the purposes of promoting an understanding of the principles of the present disclosure, reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

Embodiments disclosed herein involve a system for measuring structural features by using optical computing to directly generate autocorrelation from angle-resolved measurements. Systems disclosed herein involve angle-resolved low-coherence interferometry (a/LCI) and provides the use of optical scanning to obtain scattered light over a large angular range, high-speed Fourier domain interferometry for increasing signal throughput. Further, systems disclosed herein provide for measurement of the scattered field over two dimensions. Histological features of samples may also be extracted by use of systems disclosed herein.

In a particular application of the presently disclosed subject matter, cellular resolution images of human retina can be obtained. It is noted that the systems and methods disclosed herein may be suitably applied to obtain images and information of any other sample features.

Figure 1:
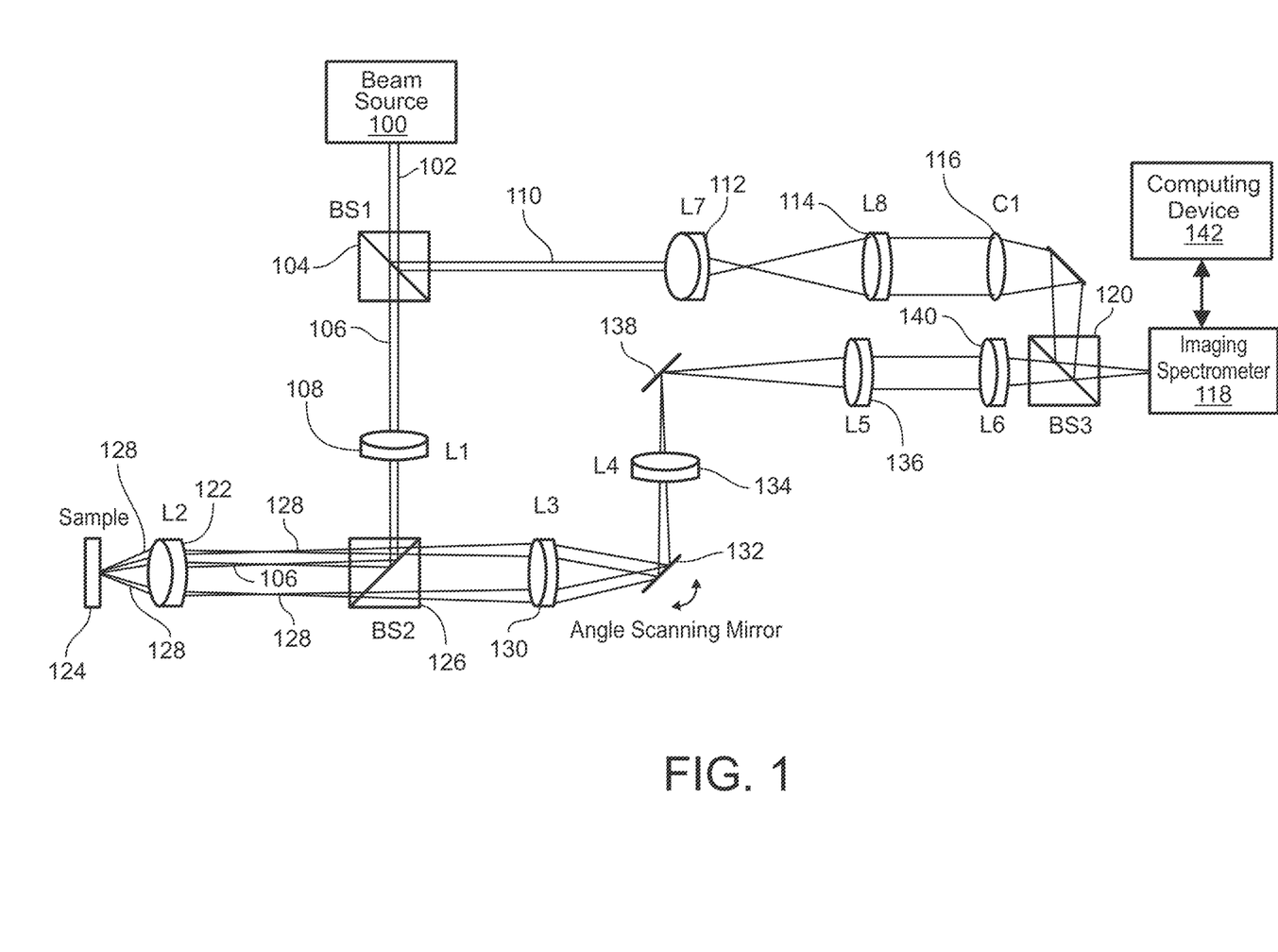
FIG. 1 is a schematic diagram of a two-dimensional, angle-resolved a/LCI system in accordance with embodiments of the present disclosure.

FIG. 1 illustrates a schematic diagram of a two-dimensional, angle-resolved a/LCI system in accordance with embodiments of the present disclosure. Although the examples herein are described as being implementing by an a/LCI system, it should be understood that the presently disclosed subject matter may be implemented by any suitable interferometer. The system is configured to implement an optical autocorrelation technique in accordance with embodiments of the present disclosure. Referring to FIG. 1, the system may include a beam source 100 configured to generate a source beam 102. The source beam 102 may be a low coherence light. The source beam 102 may be directed from the beam source 100 towards a beamsplitter (BS1) 104. The beam splitter (BS1) 104 may generate a sample beam 106 which is directed to a lens (L1) 108 and a reference beam 110 which is directed to lens (L7) 112. The width of the reference beam 110 may be modified by a pair of lenses (L7) 112 and (L8) 114. The reference beam 110 is modified from a circular beam to a cylindrical shape using a cylindrical lens (C1) 116 such that it overlaps the entrance slit to an imaging spectrometer 118, after passing through a beamsplitter (BS3) 120.

The sample beam 106 is directed to the sample by lens (L1) 108 and lens (L2) 122. Lenses (L1) 108 and (L2) 122 may function to demagnify the beam onto the sample. Lens (L1) 108 serves to focus the sample beam 106 such that lens (L2) 122 can recollimate the beam, causing the collimated beam 106 to be delivered to a sample 124 through a beamsplitter (BS2) 126. By aligning lens (L2) 122 at an offset optical axis relative to lens (L1) 108, the sample beam 106 can be delivered to the sample 124 at an oblique angle. Light 128 scattered by the sample 124 is collected by lens (L2) 122 and passed through beamsplitter (BS2) 126 to lens (L3) 130. Lenses (L2) 128 and (L3) 130 are arranged in a 4 f configuration, producing an imaging of the scattered beam which overlaps with an angle scanning mirror 132. As the angle scanning mirror 132 rotates, the angular range of the scattered beam 128. which is aligned with the optical axis, is varied. The component along the optical axis is transferred by a second 4 f configuration comprising lenses 134 (L4) and 136 (L5). A mirror 138 can direct the beam 128 from lens (L4) 134 to lens (L5) 136. another lens 140 (L6) can convert the angular distribution of the scattered sample beam 128 into a spatial distribution which overlaps with the entrance slit of the imaging spectrometer 118, after passing through beamsplitter (BS3) 120. The beamsplitter (BS3) 120 can permit crosscorrelation between the reference beam 110 and the scattered sample beam 128.

Lens pairs L3/L4 and L5/L6 can provide magnification of the beam 128. The angle scanning mirror 130 and imaging spectrometer 118 can allow detection of the scattered beam 128 in two dimensions. Thus, in this manner, the imaging spectrometer 118 may receive the scattered sample beam at a multitude of scattering angles in at least two directions. Here the different directions are defined by two distinctly different scattering planes.

It is noted that the Fourier plane of the scattered field may be overlapped with the reference field (at beamsplitter (BS3) 120). Subsequently, the scattered sample beam may be scanned onto a spectrally resolved detector allowing two-dimensional measurement of the scattered field. In this example, an imaging spectrometer and galvanometer scanner are used. However, detection can also be accomplished using any suitable type of spectrally resolved detector, including, but not limited to, a suitable spectrometer with galvanometric scanning over two dimensions, a swept source laser which changes frequency with time with galvanometric scanning over two dimensions and single detector, such as a photodiode, or a swept source laser and full field array without scanning to measure the across the scattered field.

Subsequent to detection, the resulting signal may be resolved in both spectrum and angle. This function and other processing functions described herein may be suitably implemented by a computing device 142 that is communicatively connected to the imaging spectrometer 118. The computing device 142 may be any type of device including hardware, software, firmware, the like, and combinations thereof. A computing device may include one or more processors and memory or other suitable non-transitory, computer readable storage medium having computer readable program code for implementing methods in accordance with embodiments of the present invention. The computing device 142 may include a user interface including, for example, a keyboard, a display, a mouse, and the like. Example computing devices include, but are not limited to, a laptop computer, a desktop computer, and a tablet computer.

Figure 2:
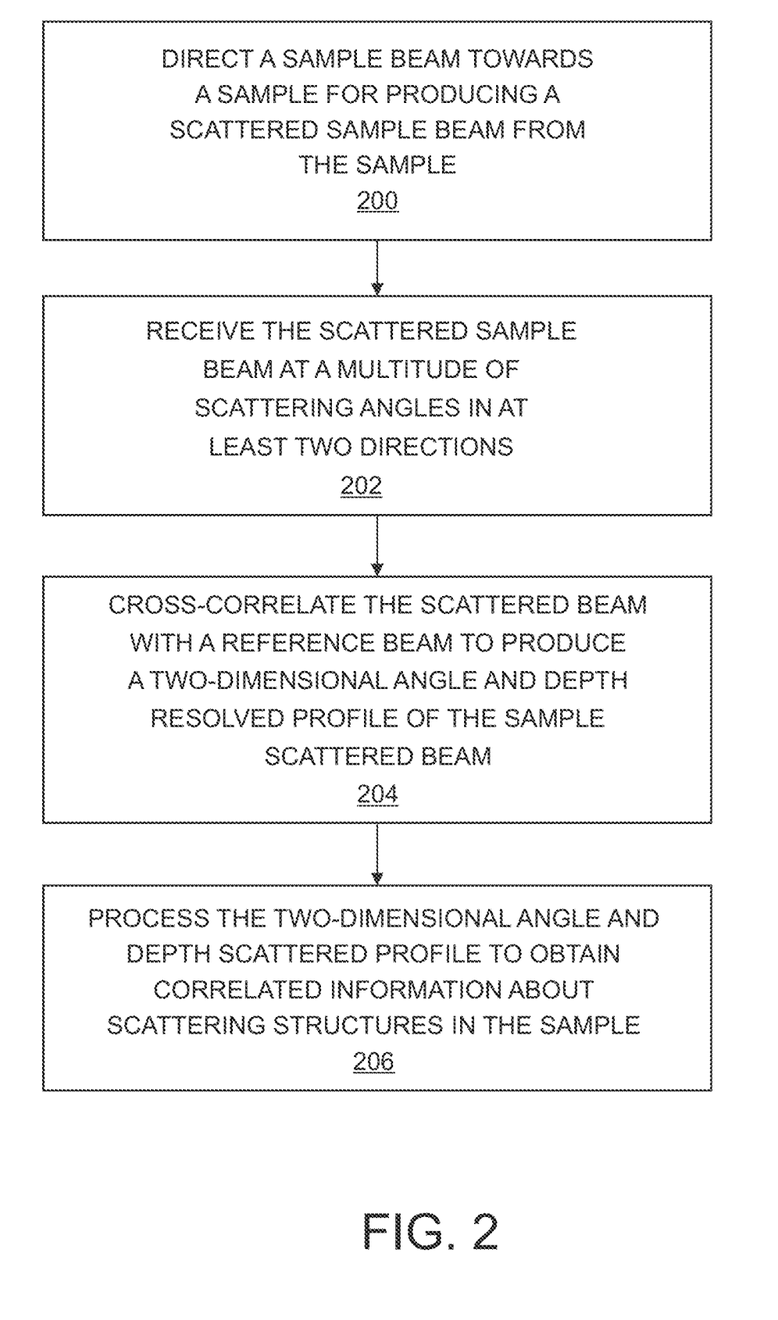
FIG. 2 is a flow chart of an example method for a/LCI based optical correlation in accordance with embodiments of the present disclosure.

In accordance with embodiments of the present disclosure, FIG. 2 illustrates a flow chart of an example method for a/LCI based optical correlation. The example method is described by example as being implemented by the system shown in FIG. 1, although it should be understood that the method may be implemented by any other suitable system. Referring to FIG. 2, the method may include directing 200 a sample beam towards a sample for producing a scattered sample beam from the sample. The sample beam may be directed to the sample at an oblique angle. Further, the sample beam may be substantially collimated. Further, the method may include receiving 202 the scattered sample beam at a multitude of scattering angles in at least two directions. For example, these steps may be implemented by the components of the system shown in FIG. 1 as described herein. The scattered sample beam may be received at the imaging spectrometer 100, for example. Data represented of the received beam may be suitably stored and communicated to the computing device 142. Steps subsequent to the directing and receiving steps 200 and 202 may be implemented by the computing device 138.

The method of FIG. 2 includes cross-correlating 204 the scattered beam with a reference beam to produce a two-dimensional angle and depth resolved profile of the sample scattered beam. For example, the reference beam in FIG. 1 may be received at the imaging spectrometer 118 and representative data of the reference beam communicated to the computing device 142. The computing device 142 may cross-correlate the scattered sample beam with the reference beam to produce a two-dimensional angle and depth resolved profile of the sample scattered beam. The scattered sample beam may be resolved in spectrum and angle. As an example, the computing device 142 may generate a signal of the magnitude of the scattered sample beam for a depth, and apply a Fourier transform to the depth resolved signal to generate a two-dimensional autocorrelation specified by radial length and direction. As described in further detail herein, the two-dimensional autocorrelation may be used to discriminate tissue by structural features for classification. The method of FIG. 2 includes processing 206 the two-dimensional angle and depth scattered profile to obtain correlated information about scattering structures in the sample. In an example, the two-dimensional autocorrelation to produce a one-dimensional correlation versus a radial distance plot. Further, for example, the one-dimensional correlation versus a radial distance plot may be used to discriminate tissue by structural features for classification.

Figure 3A:
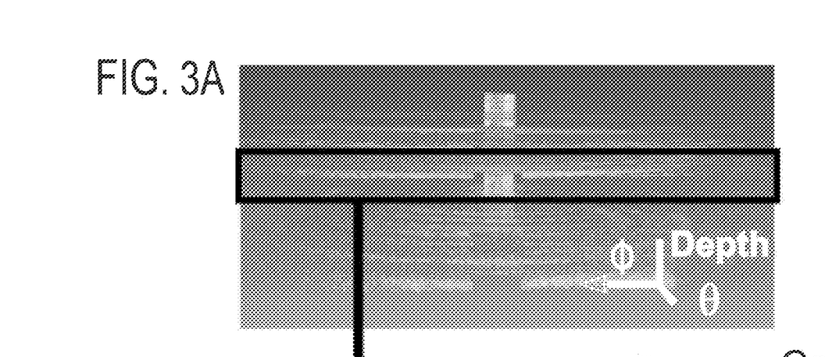
FIGS. 3A-3B depict diagrams showing a sequence of correlation processing steps in accordance with embodiments of the present disclosure.
Figure 3B:
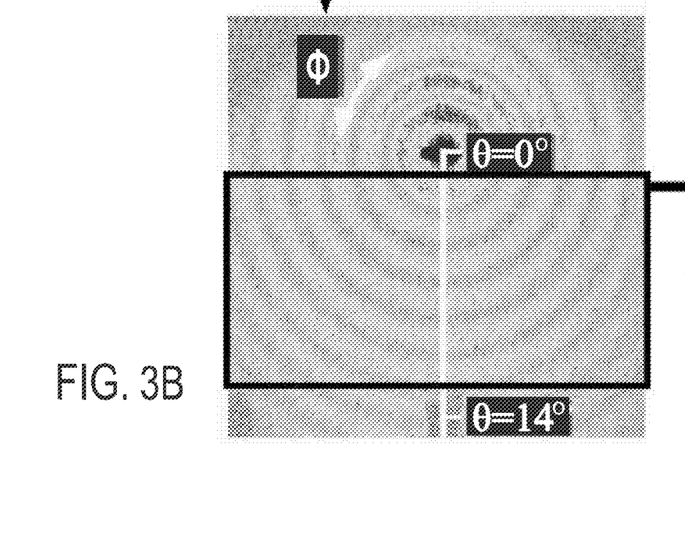
Figure 3C:
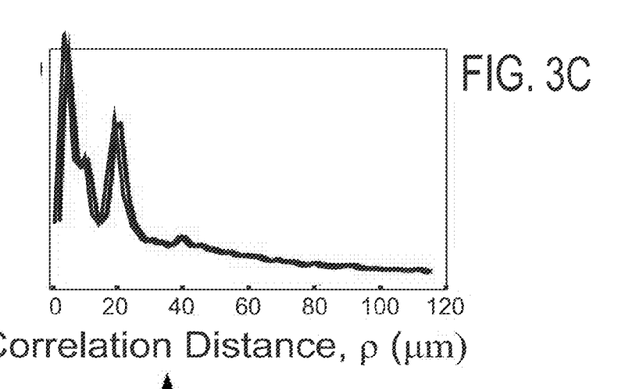
Figure 3D:
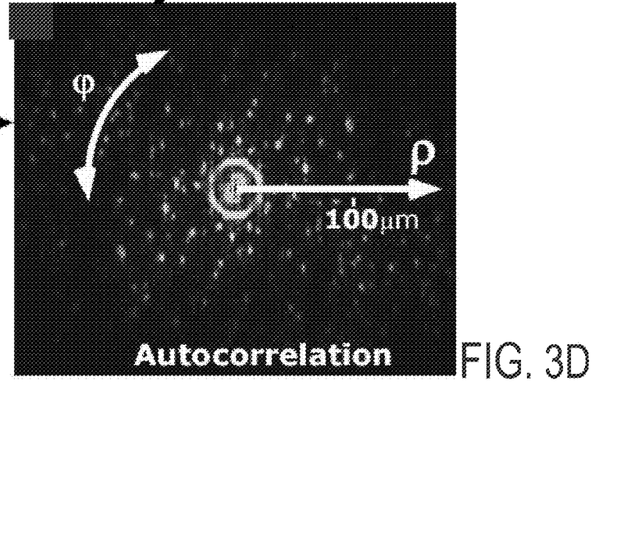

In accordance with embodiments of the present disclosure, after detection, the resulting signal corresponding to the scattered sample beam may be resolved in both spectrum and angle. Fourier transforming the spectral dimension provides axial ranging (as widely used in Fourier domain OCT), while the angle-resolved data at each depth shown in FIGS. 3A and 3B may be processed using the Fourier transform of the intensity per angle to extract the autocorrelation (shown in FIG. 3C). In accordance with embodiments of the present disclosure, FIGS. 3A-3D depict diagrams showing a sequence of correlation processing steps. Particularly, FIG. 3A is an image of a 2D angle (θ, ϕ-and-depth resolved scattered field obtained with the 2D a/LCI scan for a sample containing 20 μm diameter scatterers. FIG. 3B is an image showing a depth of interest is extracted from the a/LCI scan yielding the magnitude of the scattered field for a given depth. FIG. 3C is an image showing the scattered field for this depth being Fourier transformed to generate the 2D autocorrelation, specified by the radial length scale (ρ) and direction (ϕ). This autocorrelation plot is a representation of structure used for analysis of images generated using AO. FIG. 3D is a graph showing that the autocorrelation can be integrated over the ϕ dimension to yield a 1D correlation versus radial distance plot.

The angular distribution of scattered intensity, i.e. the squared magnitude of the field $|E(\vec{\theta})|^2$, is related to the two-point spatial correlation function of the optical field, $\Gamma_E(r)$, through a Fourier transform $$\mathfrak{I}[|E(\vec{\theta})|^2] = \int e^{jk\vec{\theta}\cdot\vec{r}} |E(\vec{\theta})|^2 d^2(k\vec{\theta}) = \langle E(\vec{r}')E^*(\vec{r}'+r\hat{\theta})\rangle = \Gamma_E(r).$$

In this expression, k is the magnitude of the optical wavevector and r is the length scale of the spatial correlations along the direction given by the angle θ. In accordance with embodiments of the present disclosure, the vector nature of the direction of the scattering angle is recognized such that measurements of the scattered field in two transverse dimensions are processed to obtain the correlation function as a function of length scales in those two dimensions.

During the analysis process, if the image of the scattered field contains aberrations such as field curvature or defocus due to the signal collection method, the scan may be numerical flattened or refocused in post processing. The result may be functionally identical or similar to autocorrelation data that may be extracted through analysis of images obtained via a suitable imaging technique, but here is the autocorrelation data is obtained via an optical transform, a method that is far less sensitive to phase errors compared with the process of direct imaging. After extraction of the 2D autocorrelation, various analysis steps are possible, including computing the 1D radial correlation, obtained by averaging the signal over the azimuthal angle (see FIG. 3C). Alternatively, the 2D correlation can be used directly to measure the anisotropy of the tissue by comparing its functional dependence on the length scale variable across different directions. In addition, if the tissue has sufficiently low anisotropy, the radial correlation can be estimated directly from 1D a/LCI measurement.

The a/LCI approach to computing the autocorrelation offers advantages over current approaches based on imaging the retina such as AO and OCT. While a/LCI can measure structures such as nuclear morphology directly, these other optical approaches involve first constructing an image and then conducting analysis of that image. Instead, a/LCI permits the same analysis using an optical transform to obtain the same information. Systems and methods disclosed herein offer several practical benefits. The fact that a/LCI directly measures structural parameters can reduce complexity compared to the approach of first imaging the structures and then analyzing that image. By using the Fourier transform property of the eye's own lens, a/LCI can directly measure the autocorrelation of photoreceptors in the retina. This approach offers a significant reduction of cost. While the cost of AO systems may restrict their use to only research applications, the relative simplicity of the a/LCI approach, comparable to an SD OCT system, can enable a widely applicable diagnostic method. Finally, the a/LCI method is not as vulnerable to aberrations and other imaging errors as direct imaging. For example in AO imaging, great effort is taken to correct imaging errors to enable illumination entering the eye to focus on as small a spot on the retina as possible to obtain cellular resolution. This is accomplished by tightly controlling the phase of light across the aperture of the eye's pupil. In a/LCI, the incident light need not be tightly focused, relaxing this constraint. Further, the scattered light returned from the retina may be analyzed by its magnitude such that the phase errors induced by these aberrations does not significantly impact the signal quality.

Figure 4A:
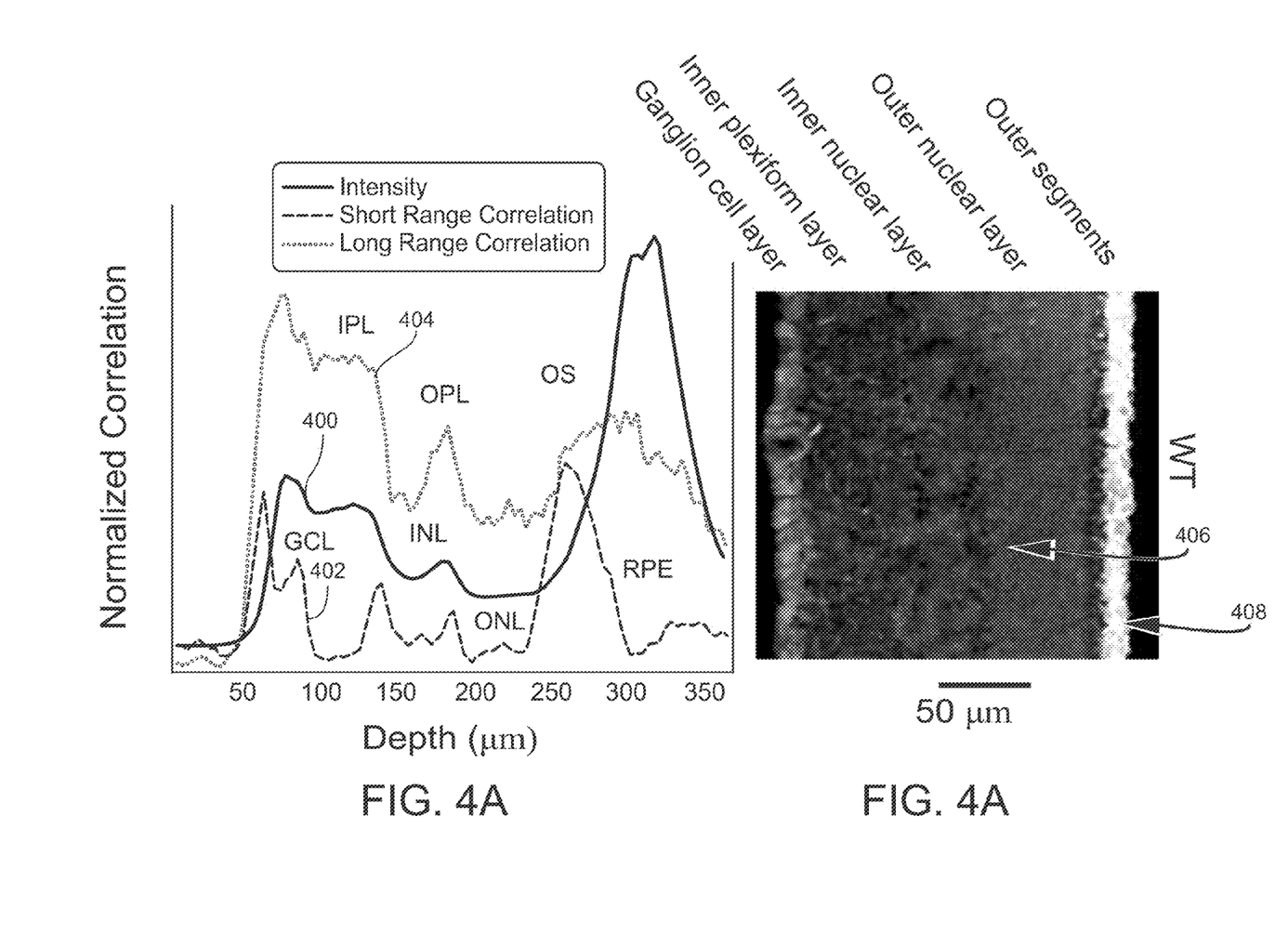
FIG. 4A is a plot of intensity, short range correlation, and long range correlation values as a function of depth within murine retinal tissue.

To demonstrate the applicability to tissue studies, ex-vivo mouse retinal tissue was scanned using the 2D a/LCI and the degree of correlation at each depth was calculated. In FIG. 4, the intensity based scan (comparable to clinical OCT) is contrasted with the short range correlation (features between 4 and 8 μm corresponding to larger cell nuclei and photoreceptors) and long range correlation (cell to cell patterns repeating on a scale larger than 30 μm). While the intensity based images provide some histological information, it is seen that the correlation data can obtain more detail. For example, the inner nuclear layer and outer segments are clearly resolved using short range correlation but not resolved in the intensity data. Conversely, the inner and outer plexiform layers, which contain longer range organization due to the presence of neural cell bodies, are clearly resolved by the long range correlation. These results demonstrate the ability of optical autocorrelation to extract histological features from intact tissue without the need for fixation or adaptive optical systems. Furthermore, the use of multiscale analysis, in which the same tissue is processed at different correlation scales reveals that a/LCI can selectively extract features unique to each retinal layer. Variations in the degree of correlation of these retinal layers is expected to reveal the presence of disease.

FIG. 4A illustrates a plot of intensity 400, short range correlation 402, and long range 404 correlation values as a function of depth within murine retinal tissue. FIG. 4B shows a confocal fluorescence image showing the same tissue showing cell nuclei (generally designated 406) and an antibody targeting peripheral nervous tissue (generally designated 408). The corresponding layers as determined by confocal microscopy are labeled on the correlation plots.

Figure 5A:
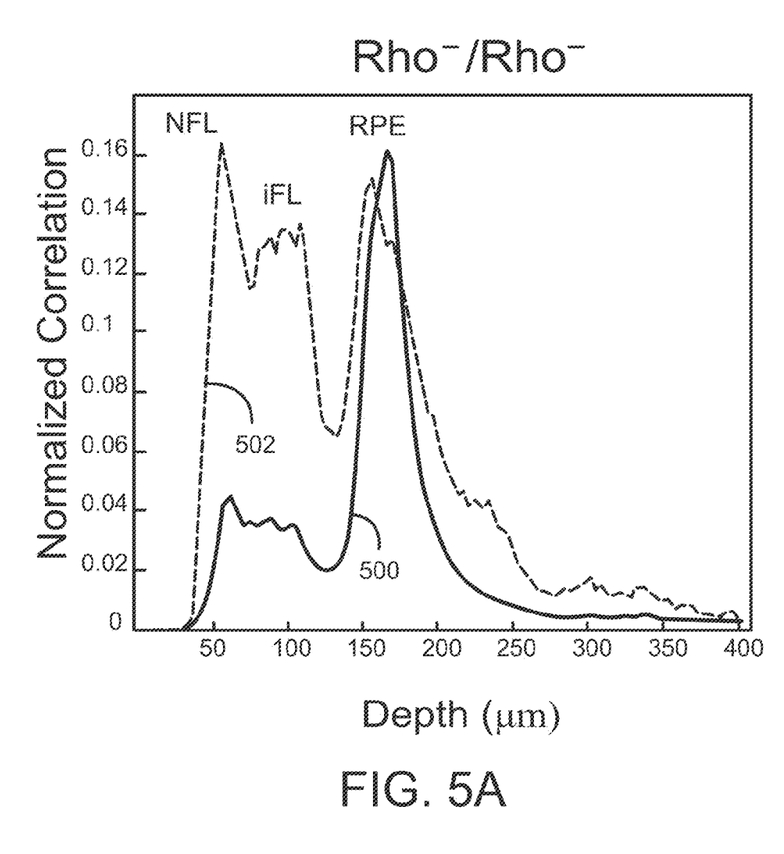
FIG. 5A shows a plot of intensity, short range correlation, and long range correlation values as a function of depth within murine retinal tissue.
Figure 5B:
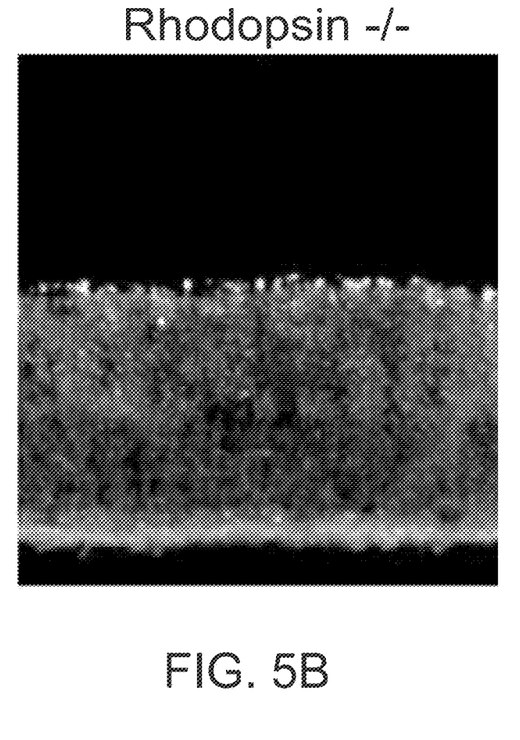
FIG. 5B shows an image of retinal tissue.

FIG. 5A shows a plot of intensity (500), short range correlation and long range correlation values as a function of depth within murine retinal tissue (502). These data are for animals with a Rhodopsin knockout gene, producing diseased retina. The correlation data shows different correlation features for the disease states. FIG. 5B shows an image of retinal tissue.

Figure 6A:
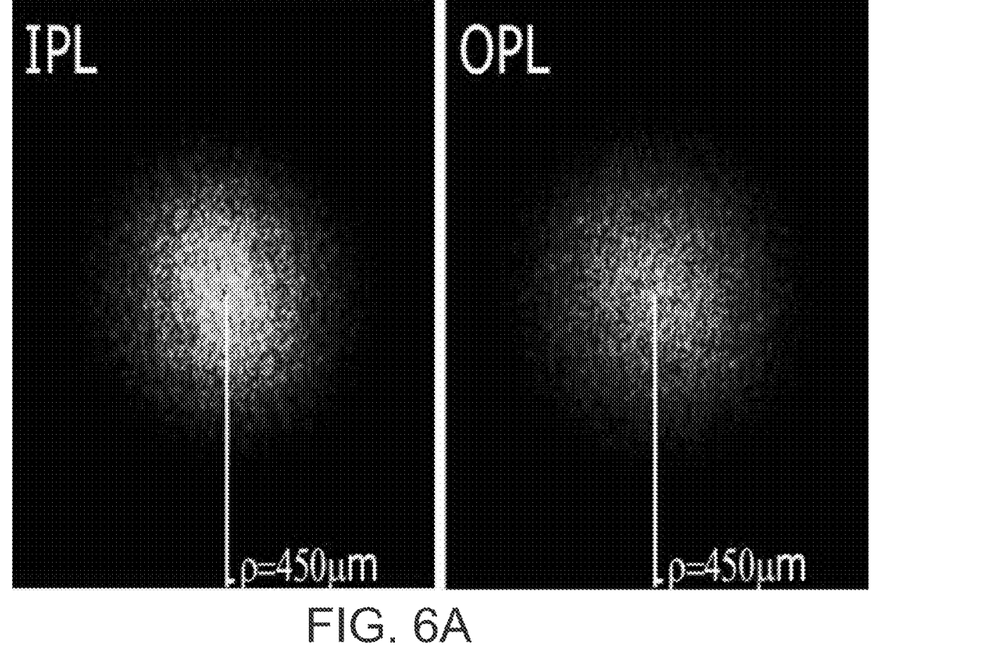
FIGS. 6A and 6B show examples of correlation plots for the IPL and OPL retinal layers.
Figure 6B:
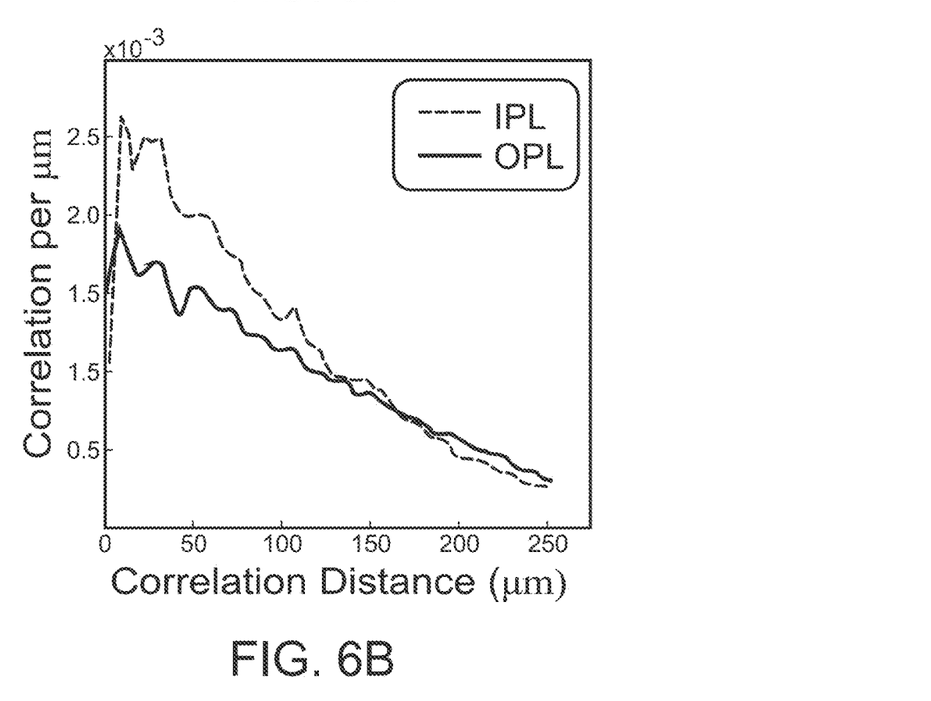

FIGS. 6A and 6B show examples of correlation plots for the IPL and OPL retinal layers. These data can be analyzed as a function of distance to analyze how correlation changes with length scale where the slope of the line or differences at key distances can be used for diagnostics. Referring to FIG. 6A, a plot is shown of correlation in two dimensions for IPL and OPL layers of the retina. Analysis as a function of correlation distance (shown in FIG. 6B), accomplished by azimuthal averaging of the plots, produces correlation as a function of radial distance.

Figure 7A:
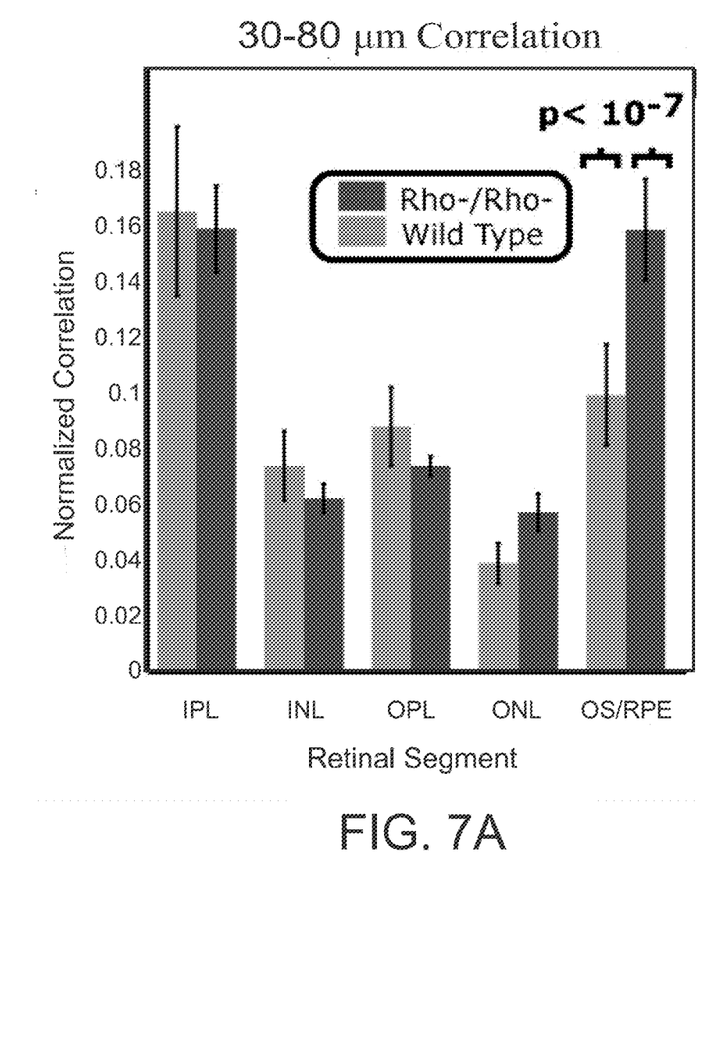
FIGS. 7A and 7B show a comparison of correlation data for length scales of 30 to 80 microns for diseased and normal mice at 6 weeks of age and 12 weeks.
Figure 7B:
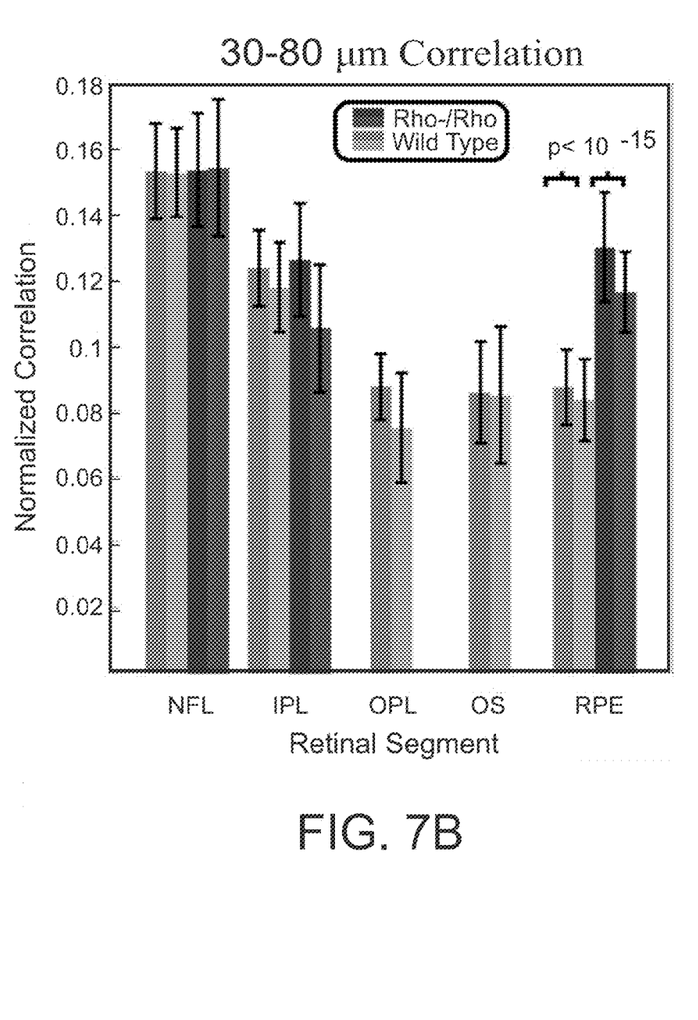

FIGS. 7A and 7B show a comparison of correlation data for length scales of 30 to 80 microns for diseased and normal mice at 6 weeks of age (FIG. 7A) and 12 weeks (FIG. 7B). Distinct changes in correlation length may be seen between disease and normal states at both time points at the OS/RPE layer. The difference becomes more distinct at later time points.

The above experiments were conducted by removing retinal tissues from animals and laying them flat for analysis on a microscope type platform. In alternative embodiments, a retinal scanner can be provided to permit scanning of animal and human retinal tissues in vivo.

Figure 8A:
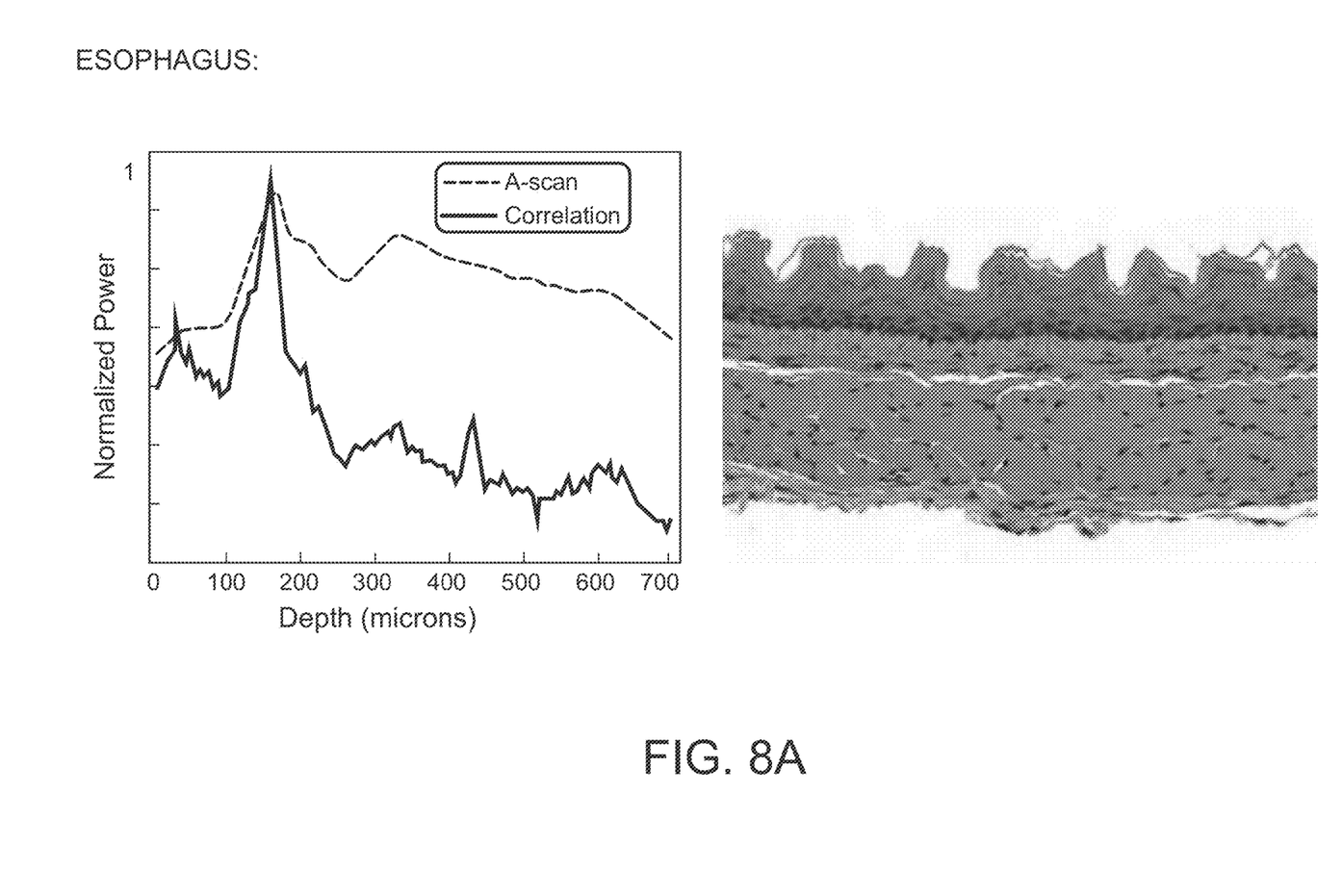
FIGS. 8A-8C show examples of correlation data for tissues of the esophagus, stomach, and colon.
Figure 8B:
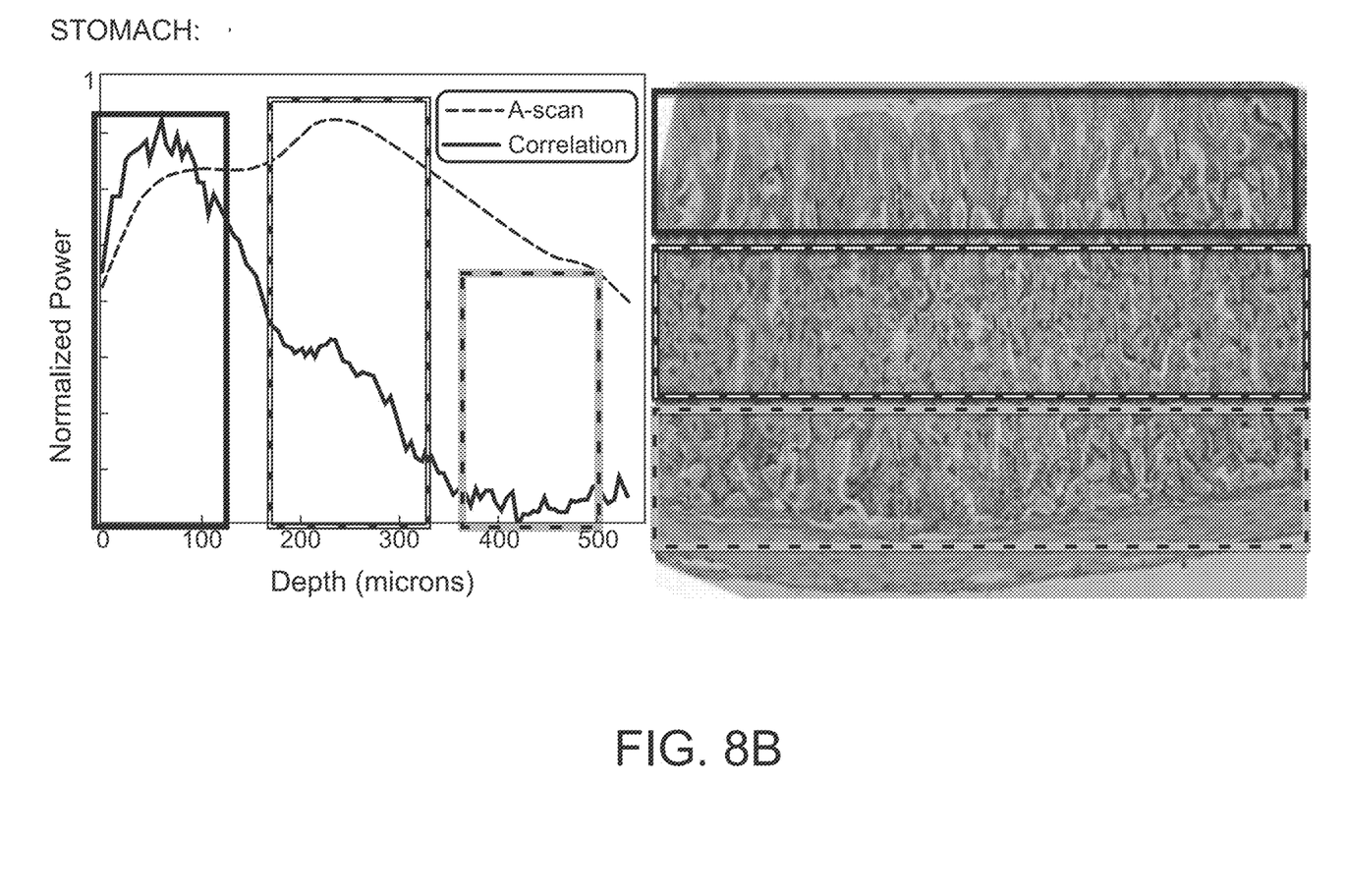
Figure 8C:
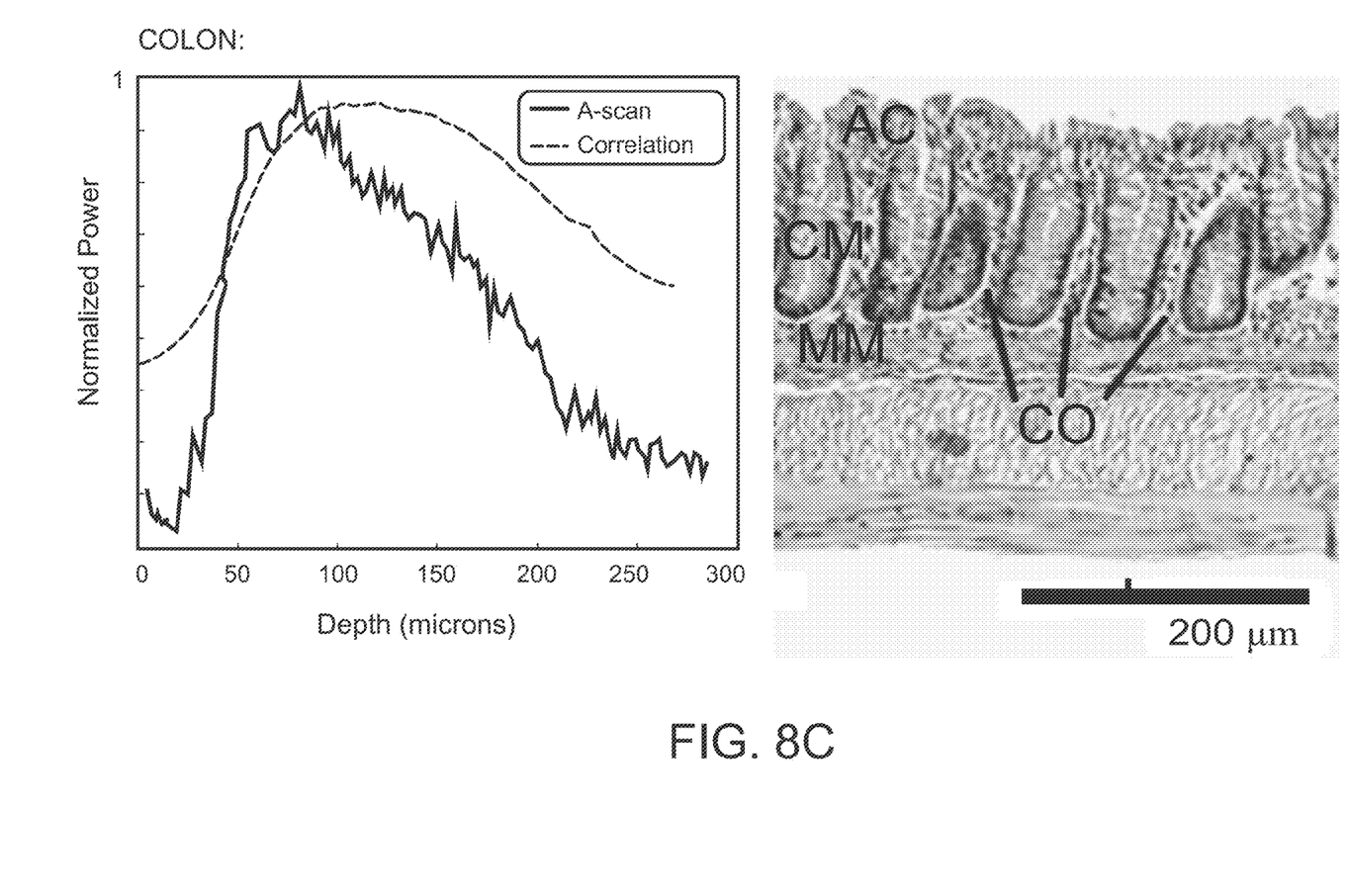

The 2D a/LCI approach for autocorrelation analysis can be used to identify structural information for other tissues as well. For example, epithelial tissues have short range and long range structures and optical measurement of the autocorrelation can reveal variations in these structures which can indicate the presence of disease, such as precancerous conditions in the esophagus, oral cavity, cervix, and colon. FIGS. 8A-8C show examples of correlation data for tissues of the esophagus, stomach and colon. Particularly, FIGS. 8A-8C show correlation data for three types of epithelial tissues. Referring to FIG. 8A, the figure shows a plot and an image of esophageal tissue with a high degree of correlation at the base of the epithelium. FIG. 8B shows a plot and image of stomach tissue with a high correlation in columnar mucus cells at surface, an increase in the middle of the tissue and low correlation at the base. FIG. 8C show a plot and image of colon tissue with a high degree of correlation at the surface, corresponding to the presence of glandular crypts. The correlation decreases abruptly at the base of the layer.

The present subject matter may be a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flow chart illustrations and/or block diagrams of methods, apparatus (systems), and computer program products according to embodiments of the subject matter. It will be understood that each block of the flow chart illustrations and/or block diagrams, and combinations of blocks in the flow chart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flow chart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flow chart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flow chart and/or block diagram block or blocks.

The flow chart and block diagrams in the Figures illustrate the architecture, functionality, and operation of possible implementations of systems, methods, and computer program products according to various embodiments of the present subject matter. In this regard, each block in the flow chart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flow chart illustration, and combinations of blocks in the block diagrams and/or flow chart illustration, can be implemented by special purpose hardware-based systems that perform the specified functions or acts or carry out combinations of special purpose hardware and computer instructions.

Any patents or publications mentioned in this specification are indicative of the levels of those skilled in the art to which the present subject matter pertains. These patents and publications are herein incorporated by reference to the same extent as if each individual publication was specifically and individually indicated to be incorporated by reference.

One skilled in the art will readily appreciate that the present subject matter is well adapted to carry out the objects and obtain the ends and advantages mentioned, as well as those inherent therein. The present examples along with the methods described herein are presently representative of various embodiments, are exemplary, and are not intended as limitations on the scope of the present subject matter. Changes therein and other uses will occur to those skilled in the art which are encompassed within the spirit of the present subject matter as defined by the scope of the claims.

What is claimed is:

1. A method of angle-resolved low coherence interferometry based optical correlation, the method comprising:
   directing a sample beam towards a sample for producing a scattered sample beam from a single fixed point on the sample;
   receiving the scattered sample beam resolved at a multitude of scattering angles in at least two directions defined by first and second scattering planes, wherein the first scattering plane is defined by an optical axis of incident light and scattered light diverging from the optical axis in a first direction, and wherein the second scattering plane is defined by the optical axis and scattered light diverging from the optical axis in a second direction that is substantially perpendicular to the first direction;
   cross-correlating the scattered sample beam with a reference beam to produce a depth resolved profile containing information about scattering in the at least two distinct scattering planes of the scattered sample beam; and
   processing the depth resolved profile to obtain correlated information about scattering structures in the sample.

2. The method of claim 1, wherein directing a sample beam towards a sample comprises directing the sample beam towards the sample at an oblique angle.

3. The method of claim 1, wherein the sample beam is substantially collimated.

4. The method of claim 1, wherein receiving the scattered sample beam comprises receiving the scattered sample beam in at least two directions at once.

5. The method of claim 1, wherein receiving the scattered sample beam comprises using an imaging spectrometer configured to receive the scattered sample beam over two dimensions.

6. The method of claim 1, wherein cross-correlating and processing comprise resolving the scattered sample beam in spectrum and angle.

7. The method of claim 1, wherein cross-correlating comprises:
   generating a signal of the magnitude of the scattered sample beam for a depth; and
   applying a Fourier transform to the depth resolved signal to generate a two-dimensional autocorrelation specified by radial length and direction.

8. The method of claim 7, further comprising using the two-dimensional autocorrelation to discriminate tissue by structural features for classification.

9. The method of claim 7, further comprising processing the two-dimensional autocorrelation to produce a one-dimensional correlation versus a radial distance plot.

10. The method of claim 9, further comprising using the one-dimensional correlation versus a radial distance plot to discriminate tissue by structural features for classification.

11. The method of claim 1, further comprising splitting a source beam into the sample beam and the reference beam.

12. A system of angle-resolved low coherence interferometry based optical correlation, the system comprising:
   an interferometry system configured to:
      direct a sample beam towards a sample for producing a scattered sample beam from a single fixed point on the sample;
      receive the scattered sample beam resolved at a multitude of scattering angles in at least two directions defined by first and second scattering planes, wherein the first scattering plane is defined by an optical axis of incident light and scattered light diverging from the optical axis in a first direction, and wherein the second scattering plane is defined by the optical axis and scattered light diverging from the optical axis in a second direction that is substantially perpendicular to the first direction; and at least one processor and memory configured to:
      cross-correlate the scattered sample beam with a reference beam to produce a depth resolved profile containing information about scattering in the at least two distinct scattering planes of the scattered sample beam; and
      process the depth resolved profile to obtain correlated information about scattering structures in the sample.

13. The system of claim 12, wherein the interferometry system is configured to direct the sample beam towards the sample at an oblique angle.

14. The system of claim 12, wherein the sample beam is substantially collimated.

15. The system of claim 12, wherein the interferometry system is configured to receive the scattered sample beam in at least two directions at once.

16. The system of claim 12, wherein the at least one processor and memory are configured to use an imaging spectrometer configured to receive the scattered sample beam over two dimensions.

17. The system of claim 12, wherein the at least one processor and memory are configured to resolve the scattered sample beam in spectrum and angle.

18. The system of claim 12, wherein the at least one processor and memory are configured to:
generate a signal of the magnitude of the scattered sample beam for a depth; and
apply a Fourier transform to the depth resolved signal to generate a two-dimensional autocorrelation specified by radial length and direction.

19. The system of claim 18, wherein the at least one processor and memory are configured to use the two-dimensional autocorrelation to discriminate tissue by structural features for classification.

20. The system of claim 18, wherein the at least one processor and memory are configured to process the two-dimensional autocorrelation to produce a one-dimensional correlation versus a radial distance plot.

21. The system of claim 20, wherein the at least one processor and memory are configured to use the one-dimensional correlation versus a radial distance plot to discriminate tissue by structural features for classification.

22. The system of claim 12, wherein the interferometry system is configured to split a source beam into the sample beam and the reference beam.

* * * * *